United States Patent [19]

Peake

[11] Patent Number: 5,730,944
[45] Date of Patent: Mar. 24, 1998

[54] FORCED WATER FILL AND DRAINAGE FOR AN UNPLUMBED STERILIZER

[75] Inventor: Steven C. Peake, Dubuque, Iowa

[73] Assignee: Barnstead/Thermolyne Corporation, Dubuque, Iowa

[21] Appl. No.: 609,860

[22] Filed: Mar. 1, 1996

[51] Int. Cl.⁶ .................................................. A61L 2/06
[52] U.S. Cl. .................................. 422/111; 422/298
[58] Field of Search .................... 422/110–116, 295, 422/298, 299, 26

[56] References Cited

U.S. PATENT DOCUMENTS

| | | | |
|---|---|---|---|
| 3,443,884 | 5/1969 | Linder | 21/93 |
| 4,759,909 | 7/1988 | Joslyn | 422/26 |
| 4,781,898 | 11/1988 | Jones | 422/295 |
| 4,865,814 | 9/1989 | Childress | 422/116 |
| 4,891,188 | 1/1990 | Albright et al. | 422/114 |
| 4,909,988 | 3/1990 | Childers et al. | 422/26 |
| 4,971,764 | 11/1990 | Albright | 422/110 |
| 5,132,084 | 7/1992 | Harrell et al. | 422/26 |
| 5,145,642 | 9/1992 | Feathers, III et al. | 422/26 |
| 5,145,647 | 9/1992 | Murray-Shelley | 422/514 |
| 5,147,613 | 9/1992 | Heilmann et al. | 422/116 |
| 5,149,507 | 9/1992 | Ellis, Jr. | 422/112 |
| 5,164,161 | 11/1992 | Feathers et al. | 422/109 |
| 5,185,709 | 2/1993 | Johnson et al. | 364/558 |
| 5,195,048 | 3/1993 | Chiffon et al. | 364/551.01 |
| 5,196,165 | 3/1993 | Harrell et al. | 422/26 |
| 5,258,921 | 11/1993 | Ellis | 364/500 |
| 5,270,948 | 12/1993 | O'Brien et al. | 364/550 |
| 5,271,893 | 12/1993 | Newman | 422/26 |
| 5,277,875 | 1/1994 | Albright et al. | 422/109 |
| 5,290,511 | 3/1994 | Newman | 422/26 |

*Primary Examiner*—Thomas G. Wyse
*Attorney, Agent, or Firm*—Wood, Herron & Evans L.L.P.

[57] ABSTRACT

An unplumbed sterilizer (10) with a self-contained heater (34, 35) has a fill system (32) that includes a pump (82) to pump liquid from a sterilizer reservoir (26) to the sterilizing chamber (22). By utilizing the pump (82) in the fill system (32), a precise volume of water is filled into the sterilizing chamber (22) with each sterilizing cycle, and further, the pump pressure flushes the fill system (32) of particles that may otherwise partially or fully clog the fill system (32). A sterilizing chamber drain cycle is executed immediately prior to the fill cycle by operating the pump (82) to pump liquid from the sterilizing chamber (22) to the reservoir (26). The operation of the drain cycle permits the fill cycle to be executed without any residual liquid in the sterilizing chamber (22); and further, the subsequent fill cycle will flush any particles from the fill system (32) introduced by the drain cycle.

15 Claims, 2 Drawing Sheets

FORCED WATER FILL AND DRAINAGE FOR AN UNPLUMBED STERILIZER

FIELD OF THE INVENTION

This invention relates generally to the field of sterilizers and, more particularly, to an improved method and apparatus for filling an unplumbed sterilizer with liquid.

BACKGROUND OF THE INVENTION

For purposes of this specification and claims, an "unplumbed sterilizer" is herein defined as a sterilizer having an internal liquid reservoir fluidly connected to a sterilizing chamber which is charged or filled with a preset volume of liquid from the reservoir. A heater operatively connected with the sterilizing chamber converts the liquid in the sterilizing chamber into a sterilizing fluid. Since the sterilizing fluid is generated within the sterilizer, an unplumbed sterilizer is not connected to an external source of steam or other sterilizing fluid. While the description herein will often refer to the liquid in the reservoir as water and the sterilizing fluid as steam, other liquids and sterilizing fluids may be used. In unplumbed sterilizers, the charging or filling of the sterilizing chamber with the preset volume of water is an important part of the sterilizing cycle. The preset amount of water is dependent on the physical characteristics of the sterilizing unit, the load, that is, of media, articles, utensils or the like to be sterilized, and the particular sterilizing cycle. Typically, in unplumbed sterilizers, often referred to as bench top sterilizers, the sterilizing chamber is physically located below or lower than the water reservoir within the sterilizer. When it is desired to fill the sterilizing chamber with water, a timer-controlled solenoid valve is opened; and gravity feeds the desired volume of water from the reservoir to the chamber during the time the solenoid valve is maintained open. While such gravity feed systems have the advantage of simplicity, they also have several inherent disadvantages.

One problem with gravity feed fill systems is the potential for contaminants to partially or fully clog the valve of the fill solenoid. Although this seldom occurs, it is potentially the most troublesome of problems. Often the source of fill valve contamination is the articles or media being sterilized. During the sterilization process, some media may evaporate from a culture; and when the sterilizing chamber is vented back to the reservoir, the media condenses into the reservoir water. During subsequent fill cycles, small particles of media or other contaminants which are in the fill water can become lodged in the fill solenoid valve and restrict the flow of water into the sterilizer while the valve is open. Since the fill cycle is timer-controlled, restrictions in the fill valve will result in the sterilizing chamber being filled with less than the desired volume of water. The smaller volume of water presents a smaller load to the heaters that convert the water to steam, and therefore, the heaters may overheat. The heaters have over-temperature protection, that is, high temperature thermostats, to turn the heaters OFF in the event of overheating. However, continued operation of the heaters at the over-temperature limit is detrimental to the life of the heaters. Further, to remove the valve contamination may require some disassembly of the sterilizer which is inconvenient and time consuming.

Another problem with some gravity feed systems is the variation in reservoir head pressure from different levels of water in the reservoir. After the reservoir is filled, the level of water in the reservoir continuously drops with subsequent sterilizing cycles. When the reservoir reaches a low water limit, the reservoir is refilled. Different water levels in the reservoir produce correspondingly different head pressures during the gravity feed fill cycle of the sterilizing chamber. Therefore, executing the constant time water fill cycles with different water levels in the reservoir will result in different volumes of water being filled into the sterilizing chamber. Overfilling of the sterilizing chamber can result in overflow, or spillage when the door of the sterilizer is opened, or difficulties in drying. Conversely, under-filling, or a short fill of water in the sterilizing chamber, causes the heating element to overheat. As illustrated in U.S. Pat. No. 4,865,814, this problem can be eliminated by providing a second water reservoir that is used for filling the sterilizing chamber with water. Before any fill cycle is executed, the second reservoir is filled, thereby guaranteeing that each fill cycle will fill the sterilizing chamber with the same volume of water. However, the use of a second reservoir has several disadvantages. First, the time required to fill the second reservoir increases the overall sterilizing cycle time. Second, the provision for a second reservoir and the associated valves and plumbing increases the overall cost of the sterilization device.

A still further problem relates to the drainage of water from the sterilizing chamber after a sterilizing cycle. The desired volume of water filled into the sterilizing chamber is a volume that, to the greatest extent possible, will be converted into steam so that a minimum of water remains in the chamber after the sterilizing cycle. However, with successive sterilizing cycles, liquid contained in the material being sterilized may be evaporated from the material and condensed within the sterilizing chamber. Alternatively, during a sterilization cycle, all of the liquid filled into the chamber may not be converted into sterilizing steam. In either case, the result is that liquid remaining from prior sterilizing cycles can accumulate within the sterilizer; and over a number of sterilizing cycles, the liquid accumulation can result in liquid overflowing or running out of the sterilizer when it is opened to remove the sterilized material. Such an overflow is a significant inconvenience.

To avoid or minimize the problem of such water accumulation and overflow, immediately after the completion of the sterilizing cycle, many sterilizers open the fill solenoid valve, and the pressure in the sterilizing chamber causes any water that remains in the sterilizing chamber to be forced back through the fill line, through the fill valve and into the reservoir. While this reverse flush of water through the fill line is effective in removing the excess water, it does present problems of its own. For example, if the water that has accumulated in the bottom of the sterilizing chamber is contaminated with particles of the media being sterilized, that contamination can accumulate in the fill line or in the fill valve, potentially clogging either the fill line or the fill valve. Further, if the sterilizer is not used again for a period of time, for example, overnight, the media that has accumulated in the fill line or the fill valve will harden, which will prevent it from being flushed or washed away by the next fill cycle. Media that has hardened in the fill line or fill valve often must be physically removed, requiring the partial disassembly of the sterilizer for cleaning. Such a cleaning operation is a substantial inconvenience to the user.

From the above, it is clear that sterilizers having gravity feed fill cycles exhibit several deficiencies which may lead to the over-filling or under-filling of water into the sterilizing chamber with the consequential disadvantages of either water spillage or high temperature heater operation which reduces the useful life of the heater. Further, known attempts to provide a more consistent water fill volume have the disadvantages of a longer fill cycle time and increased cost and complexity in the sterilizer design. Consequently, there is a need to provide an improved, more efficient and reliable apparatus and method for filling for an unplumbed sterilizing chamber with water. In addition, known drainage techniques for removing water after a sterilizing cycle have the disadvantage of potentially restricting or clogging the fill line or fill valve. Consequently, there is a need for providing a better, more reliable drainage system for the sterilizing chamber.

SUMMARY OF THE INVENTION

The present invention provides an unplumbed sterilizer provided with a self-contained heater, that fills the sterilizing chamber with a desired volume of water from a reservoir without underfilling or overfilling. Further, the unplumbed sterilizer of the present invention reliably and repeatedly fills the sterilizing chamber with the desired volume of water during successive sterilizing cycles without overfilling or underfilling. The volume of water input to the sterilizing chamber is independent of variations of water level in the reservoir and further operates more reliably to provide the desired water fill in the presence of contamination in the fill line or the fill valve. In addition, the sterilizer of the present invention drains excess water from the sterilizing chamber prior to a fill cycle so that the fill cycle cleans the fill system of particulate matter remaining from the drain cycle, thereby minimizing the potential for uneven fills and more consistently filling the sterilizing chamber with a known volume of water. Therefore, the unplumbed sterilizer of the present invention has the advantages of operating more reliably and being self cleaning so that partial disassembly and physical cleaning is generally not required.

In accordance with the principles of the present invention and in accordance with the described embodiments, the unplumbed sterilizer includes a chamber for receiving items to be sterilized which has an inlet for receiving water. A heater is operatively connected to the chamber for heating the water to produce the steam used for sterilization. A pump is fluidly connected to the reservoir. A control operates the pump in a predetermined controlled manner to pump a predetermined volume of water from the reservoir into the sterilizing chamber. In another aspect of the invention, an electro-mechanical valve with a flow restricting orifice is located between the pump and the sterilizing chamber.

In another embodiment of the invention, the control provides a method of operation in which a control signal operates the pump to pump the desired volume of water into the sterilizing chamber. In one aspect of the invention, the pump is operated for a predetermined period of time. In another aspect of the invention, a positive displacement pump is operated over a predetermined pump cycle of operation. In a still further aspect of the invention, the control opens a valve with an orifice or flow restrictor that is located between the pump and the sterilization chamber. The pump operates at a known pressure to pump the water through a flow restricting valve orifice of a known size over a predetermined period of time, thereby providing a desired volume of water to the chamber.

The pump consistently and reliably provides the same volume of water to the chamber over successive fill cycles. With the pump, the desired volume of water is provided to the chamber in much less time than with gravity feed systems and is independent of variations in head pressure within the reservoir itself. Further, the pressure of the pump is effective to unclog the valve of any contaminant particles that may have lodged therein. Therefore, the water fill system for a sterilizer utilizing the pump has the advantages of providing shorter and more accurate water fill cycles that, in turn, result in more efficient and reliable sterilizer operation by eliminating the adverse effects of underfilling or overfilling the sterilizing chamber. The water fill system utilizing the pump has the advantage of being generally self cleaning.

In another embodiment of the invention, the control executes a drain cycle immediately prior to the above-described fill cycle and may be considered a part of the fill cycle. Upon initiating the drain cycle, the solenoid valve is opened; and the pump is operated to produce a pressure differential that forces water remaining from a previous sterilizing cycle from the chamber, through the open fill valve and back into the reservoir. The drain cycle removes accumulated liquid from the chamber so that each fill cycle is started with a known and predictable quantity of water in the chamber. Depending on the location of the physical drain within the chamber, the known quantity of water may be little or none. Therefore, the invention has the advantage of preventing overflow from accumulated water. In addition, knowing the quantity of water with which the fill cycle starts, permits a more predictable and reliable fill cycle with the advantages previously discussed.

Further, if the drain cycle introduces any particles or other contaminants into the fill line and the fill valve, the execution of a fill cycle immediately after the drain cycle is effective to wash such contamination out of the fill line and the fill valve before it has an opportunity to coagulate or harden. Therefore, the invention has the advantage of providing even more reliable operation because the drain cycle is self-cleaning.

These and other objects and advantages of the present invention will become more readily apparent during the following detailed description together with the drawings herein.

DETAILED DESCRIPTION OF THE INVENTION

Figure 1:
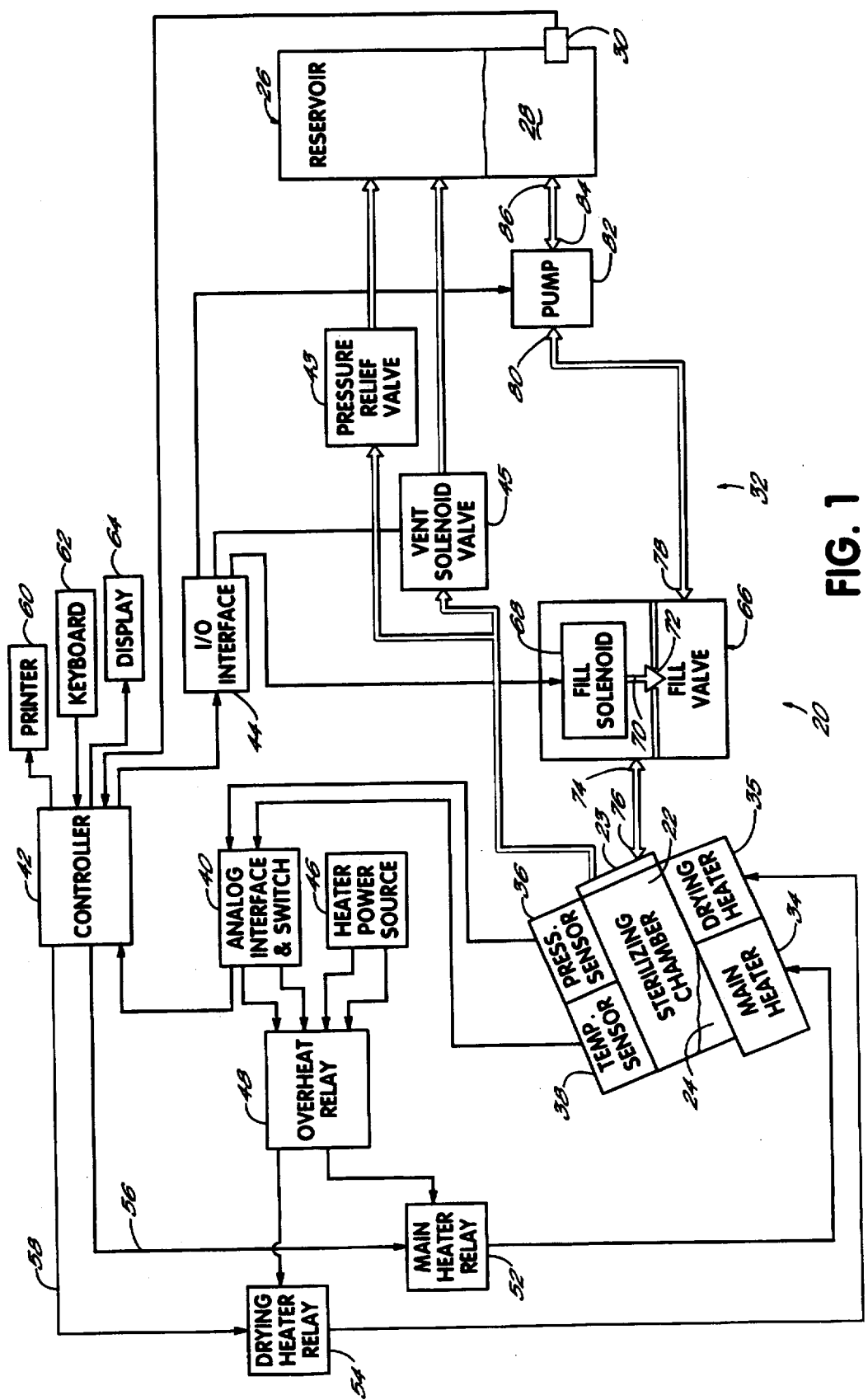
FIG. 1 is a schematic block diagram of a sterilizer constructed in accordance with the principles of the present invention.

Referring to FIG. 1, a sterilizer 20 has a sterilizing chamber 22 having a hinged door 23 on the front thereof through which articles or material to be sterilized are placed into and removed from the sterilizing chamber 22. Often, the sterilizing chamber 22 is mounted at a slight incline with respect to the horizontal so that any liquid within the sterilizing chamber will flow to the rear bottom portion 24 of the sterilizing chamber 22. The sterilizer 20 further includes a reservoir 26 which is filled with water 28. The reservoir can be filled manually or is filled automatically in response to outputs from a water level detection switch 30 that detects high and low water levels within the reservoir 26.

Prior to a sterilizing cycle, a volume of water is transferred from the reservoir 26 through a fill system 32 and into the sterilizing chamber 22. The water collects at the bottom rear section 24. A main, steam generating electrical heater 34, which is in the range of 1500 watts, is turned on to vaporize the water into sterilizing steam which pressurizes the sterilizing chamber 22 and sterilizes items within the chamber 22. An electrical drying heater 35, in the range of 400 watts, is used to dry the sterilized articles or material in a known manner. A pressure sensor 36 and a temperature sensor 38 provide respective pressure and temperature output signals to an analog interface and switch circuit 40 that, in turn, provides the temperature and pressure signals to a controller 42. The controller 42 is preferably a microprocessor-based programmable controller with arithmetic and logic capabilities. The controller 42 controls the sterilizing cycle in accordance with the temperature and pressure output signals. In addition, a pressure relief valve 43 will respond to excessively high pressure in the sterilizing chamber 22 and open the chamber to the reservoir 26 in response to the pressure exceeding the pressure relief valve setting. In a known manner, the controller 42 provides a control signal to an I/O controller 44 to operate a vent solenoid valve 45 at the end of the sterilizing cycle to vent the sterilizing steam back to the reservoir.

A heater power source 46, for example, a source of AC power, is connected to an overheat relay 48. Under normal conditions, the overheat relay 48 is operated by the circuit 40 to connect power from the heater power source 46 to a main heater relay 52 and drying heater relay 54. The relays 52, 54 are preferably solid state relays and have input control signals connected to outputs of the controller 42. If the controller provides a main heater ON signal on line 56, the main relay 52 closes connecting power to the main heater 34. Similarly, if the controller 42 provides a drying heater ON signal on line 58, the drying heater relay 54 connects heater power to the drying heater 35. A printer 60, keyboard 62 and display 64 may be connected to the controller 42 depending upon the requirements of the sterilizer 20. The keyboard 62 is used by an operator to provide process information to the controller 42. For example, parameters for different types of sterilization cycles with associated pressures, temperatures and timing parameters can be input or programmed into the controller 42 using the keyboard 62. The display 64 is used to display the information being input by the operator and also displays the active cycle and associated parameters during a sterilization cycle. The printer 60 can be used to print out the process variable values that are used during a sterilization cycle.

The water fill system 32 of the present invention utilizes an electro-mechanical valve 66 having a solenoid 68 operating a valve stem 70 that selectively opens and closes a flow restricting orifice 72 within the fill valve 66. The fill valve 66 has a first port 74 connected to an inlet 76 of the sterilizing chamber 22. Further, the fill valve 66 has a second port 78 connected to a first port 80 of a pump 82. The pump 82 has a second port 84 connected to an outlet of the reservoir 86. Therefore, the fill system 32 provides a fluid connection from the reservoir 26 through the pump 82 through flow restricting orifice 72 of the fill valve 66 to the sterilizing chamber 22. The operation of the solenoid 68 and pump 82 are controlled by the controller 42, providing respective control signals to the I/O interface 44 which in turn is connected to the pump 82 and the solenoid 68.

In use, the sterilizer 20 has the capability of executing many different sterilizing cycles depending on the articles or media to be sterilized. In each of those sterilizing cycles, it is necessary for the sterilizing chamber 22 to be filled with a precise volume of water which the main heater 34 converts to sterilizing steam. Variations in the size of that volume of water adversely affect the operation of the sterilizer and the sterilizing process. For example, a "short-fill", which is less than the desired volume of water filled into the chamber 22, provides less than the desired thermal load for the main heater 34. Consequently, the main heater 34 may overheat, causing the overheat relay 48 to disconnect power from the main heater relay 52, thereby interrupting the sterilizing cycle. Further, continued overheating of the main heater 34 will shorten its useful life. On the other hand, providing too great a volume of water to the sterilizing chamber 22 may require a longer time for the main heater 34 to convert the water to steam, may reduce the quality of the steam for sterilization purposes and/or may saturate the media being sterilized. Therefore, providing the precise volume of water to the sterilizing chamber is important for consistent and reliable high quality sterilizing cycles.

Figure 2:
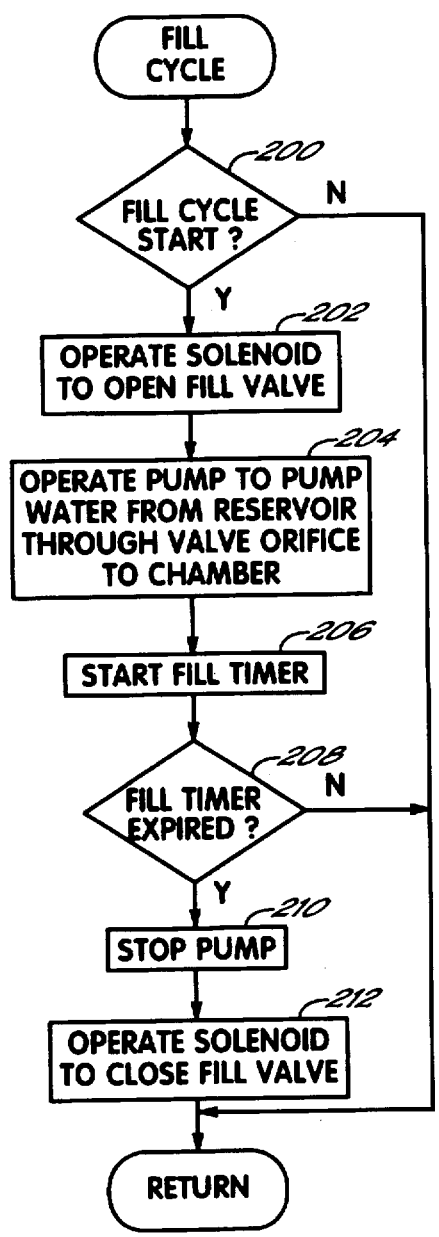
FIG. 2 is a flow chart of a subroutine illustrating the steps of a water fill cycle in accordance with the principles of the present invention.

FIG. 2 illustrates the steps of a water fill cycle in accordance with the principles of the present invention. FIG. 2 is representative of a process that is executed within the operating program of the controller 42. The subroutine of FIG. 2 at 200 awaits the command to begin a water fill cycle. The command may represent the setting of a flag or other state within the controller 42 in response to running a sterilizing cycle. Further, the command may be generated by an operator input through the keyboard 62. If no fill cycle start is detected the water fill cycle subroutine returns to the main program and remains inactive. Upon detecting a fill cycle start, the subroutine at 202 will cause the controller 42 to produce a signal through the I/O interface 44 to the solenoid 68 to operate the solenoid 68 so that the flow restricting orifice 72 of the fill valve 66 is opened. Thereafter, the subroutine at 204 will cause the controller 42 to produce another output signal to the I/O interface 44 which is also connected to the pump 82. The controller 42 turns the pump 82 ON so that the pump 82, which is preferably a diaphragm pump, produces a pressure and pumps water from the reservoir 28 through the pump 82 to the fill valve 66. The pressure produced by the pump 82 and the diameter of the orifice 72 are known; and therefore, the period of time that the pump must operate to provide the desired volume of water within the sterilizing chamber 22 is readily determined. The operating time of the pump is measured by the system by the subroutine at 206, simultaneously with starting the pump 82, starting a fill timer immediately after turning the pump 82 ON. Thereafter, on a periodic basis, the subroutine at 208 checks whether the fill timer has expired. When the subroutine at 210 detects the expiration of the fill timer, the controller 42 changes the signal to the I/0 interface 44 to turn the pump 82 OFF. Thereafter, at 212, the controller changes the state of the signal to the I/O interface 44 to operate the solenoid 68 to close the orifice 72 within the fill valve 66. Preferably, the pump 82 is a small diaphragm pump that produces a pressure in the range of approximately 8–15 pounds per square inch ("psi").

By utilizing the pump 82 within the fill system 32, the volume of water filled into the sterilizing chamber 22 can be more accurately controlled not only within a single fill cycle but over successive fill cycles. Further, the pump pressure will result in the sterilizing chamber being filled with the desired volume of water in approximately 15–20 seconds. With a gravity feed system, a comparable fill cycle duration is often 60–90 seconds. Therefore, the pump 82 permits shorter water fill cycle that with resulting advantage of a more efficient sterilizing cycle. In addition, the pressure produced by the pump is effective to dislodge particles or other contaminants that may have collected around the orifice 72 that would otherwise restrict flow of the water through the orifice 72. Therefore, the fill system 32 utilizing the pump 82 has a self cleaning capability. The fill system 32 has the advantages of providing the sterilizer 20 with a more reliable operation and potentially a longer life.

If successive sterilizing cycles are run for liquid loads, the drying heater 35 is not used, and the sterilizing process will often evaporate liquid from the load and condense that liquid in the sterilizing chamber. With successive sterilizing cycles, the liquid from previous sterilizing cycles may accumulate within the sterilizing chamber to the point that it overflows when the door 23 on the sterilizing chamber 22 is opened. Further, the accumulation of liquid in the sterilizing chamber with successive sterilizing cycles changes the volume of liquid to be converted to steam which may affect the quality of sterilizing steam produced by the heater 34.

Figure 3:
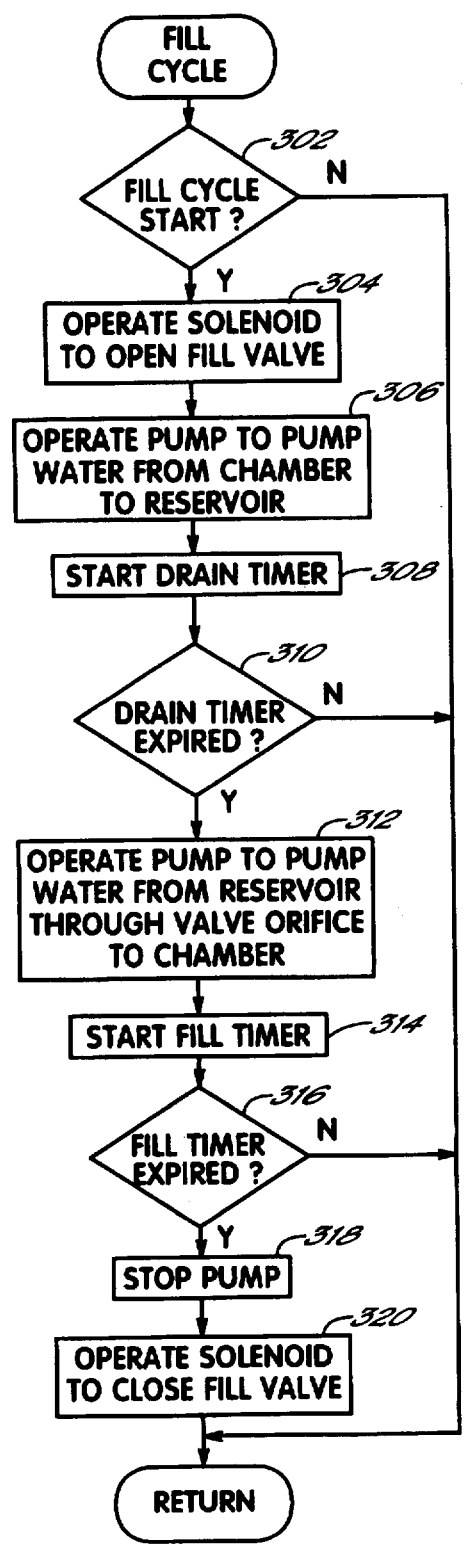
FIG. 3 is a flow chart of a subroutine illustrating the steps of a fill cycle including a drain cycle.

To overcome the problem of liquid collecting in the sterilizing chamber over successive cycles, the water fill cycle has a second embodiment illustrated in the flow chart of FIG. 3. In a manner identical to that previously described, the controller 42 executing the subroutine of FIG. 3 at 302 and 304 detects the start of a fill cycle and operates the solenoid 68 to open the orifice 72 of the fill valve 66. Next, at 306, the controller 42 provides a signal to the I/O interface 44 to turn the pump 82 ON so that a pressure is created to pump the liquid from the sterilizing chamber 22 through the orifice 72 of the fill valve 66 and into the reservoir 26. That action, in essence, starts a drain cycle in which liquid is drained under pressure from the sterilizing chamber 22. The controller at 308 simultaneously with starting the pump 82 starts a drain timer; and thereafter, at 310, the controller periodically checks whether the drain timer has expired. Upon expiration of the drain timer, the controller 42 proceeds to execute the steps 312–320 of the subroutine of FIG. 3. Those steps are identical to the previously described steps 204–212 with respect to FIG. 2 and operate to fill the reservoir with a predetermined volume of water for the next sterilizing cycle.

By using the pump to drain liquid from the sterilizing chamber, the sterilizing chamber always has the identical volume of liquid in it prior to initiating a fill cycle. That volume may range from no liquid to a small volume of liquid depending on the location of the inlet 76 with respect to the lowest point in the area 24 of the sterilizing chamber 22. Consequently, the utilization of a pressurized drain cycle provides for more consistent fill cycles as well as a more consistent sterilizing process. In addition, the drain cycle drains the accumulation of water within the sterilizing chamber, and therefore eliminates the potential for overflow from the chamber upon opening the door. Further, by executing the drain cycle immediately prior to the fill cycle, any particles that are brought into the fill system 32 by the drain cycle are immediately flushed back out of the fill system 32 by the subsequent fill cycle. Therefore, the unique combination of drain cycle-fill cycle has the advantage of self cleaning the fill system 32.

While the invention has been set forth by a description of the preferred embodiment in considerable detail, it is not intended to restrict or in any way limit the claims to such detail. Additional advantages and modifications will readily appear to those who are skilled in the art. While the pump 82 is preferably a diaphragm pump, other types of pumps, for example, a gear pump, a vane pump or other positive displacement pump may be used.

Further, if pump 82 is a positive displacement pump, the valve 66 having the flow restricting orifice 72 can used as previously described. However, alternatively, the flow restricting orifice 72 in the valve 66 can be eliminated because the head pressure of a positive displacement pump is sufficiently constant to provide the desired liquid fill from the reservoir 26 to the sterilizing chamber 22 over a cycle of operation. Alternatively, the solenoid operated fill valve 66 described with respect to FIG. 1 could be replaced with a motorized ball valve or other remotely controllable valve. In another embodiment utilizing a positive displacement pump, for fill cycle operations, the valve 66 could implemented with a simple check valve that operates as a function of pressure differentials and is not operated by the controller 42.

Since a positive displacement pump provides a liquid volume output that is proportional and linear to the pump operation, the preset volume of liquid can be controlled by operating the positive displacement pump over a predetermined period of time. In that case, the a fill timer as described in steps 206, 208 of FIG. 2 and steps 314, 316 of FIG. 3 can be used to measure a predetermined period of time for operating the positive displacement pump. Alternatively, as will be appreciated, the operation of fill timers can be replaced by operating cycle counters that are operative to command operation of the positive displacement pump over whole or partial pump cycles. Further, the pump control can be open loop, in that the pump is commanded to operate through one or more whole or partial cycles. Alternatively, the controller 42 can control the pump as a function of a feedback signal derived from the pump operation in which the feedback signal represents a measure of angular or linear motion of the positive displacement pump. The above also applies to using the positive displacement pump to drain the sterilizing chamber as described at steps 306–310 of FIG. 3.

The pump 82 has a preferred pressure range of approximately 5–40 pounds per square inch {"psi"}, however, a fill cycle could be performed with a pressure head as low as 2–3 psi. The controller 42 can also operate with the water level detection switch 30 and a fill valve (not shown) connected to a liquid supply to automatically maintain the reservoir filled with a desired level of liquid or water. The invention, therefore, in its broadest aspects, is not limited to the specific details shown and described. Consequently, departures may be made from the details described herein without departing from the spirit and scope of the claims which follow:

What is claimed is:

1. An unplumbed sterilizer comprising:

a reservoir holding a liquid and having a reservoir inlet and a reservoir outlet;

a sterilizing chamber for receiving a load to be sterilized and having a sterilizing chamber inlet for receiving the liquid;

a heater operatively connected to the sterilizing chamber for heating the liquid in the sterilizing chamber to create a sterilizing fluid;

a pump fluidly connected between the reservoir outlet and the sterilizing chamber inlet; and a controller operatively connected to the pump and providing signals to operate the pump in a predetermined controlled manner to pump a predetermined quantity of liquid from the reservoir to the sterilizing chamber.

2. The unplumbed sterilizer of claim 1 further comprising a valve having a first valve port in fluid communication with a pump outlet and a second valve port in fluid communication with the sterilizing chamber inlet.

3. The unplumbed sterilizer of claim 2 wherein the pump is a positive displacement pump.

4. The unplumbed sterilizer of claim 2 further comprising an electro-mechanical valve having a flow restricting orifice, a first valve port in fluid communication with a pump outlet and a second valve port in fluid communication with the sterilizing chamber inlet and the controller is connected to the electro-mechanical valve to operate the valve in a predetermined controlled manner.

5. The unplumbed sterilizer of claim 4 wherein the pump is a diaphragm pump.

6. The unplumbed sterilizer of claim 1 wherein the pump produces a pressure in the range of approximately 2–40 psi.

7. The unplumbed sterilizer of claim 4 wherein the controller provides a first signal to operate the electro-mechanical valve and open the flow restricting orifice.

8. The unplumbed sterilizer of claim 7 wherein the controller provides a second signal to operate the pump to pump liquid from the sterilizing chamber into the reservoir.

9. The unplumbed sterilizer of claim 8 wherein the controller provides the second signal for a predetermined period of time.

10. The unplumbed sterilizer of claim 7 wherein the controller provides a third signal to operate the pump to pump liquid from the reservoir into the sterilizing chamber.

11. The unplumbed sterilizer of claim 10 wherein the controller provides the third signal for a predetermined period of time.

12. The unplumbed sterilizer of claims 9 or 11 wherein the controller provides a fourth signal to operate the electro-mechanical valve and close the flow restricting orifice.

13. The unplumbed sterilizer of claim 12 wherein the controller provides the third signal after the first signal but before the second signal.

14. An unplumbed sterilizer comprising:

a reservoir holding a liquid and having a reservoir inlet and a reservoir outlet;

a sterilizing chamber for receiving a load to be sterilized and having a sterilizing chamber inlet for receiving the liquid;

a heater operatively connected to the sterilizing chamber for heating the liquid in the sterilizing chamber to create a sterilizing fluid;

a pump having a pump inlet fluidly connected to the reservoir outlet;

an electro-mechanical valve having a flow restricting orifice, a first valve port fluidly connected to the reservoir outlet and a second valve port fluidly connected to the sterilizing chamber inlet; and a controller operatively connected to the electro-mechanical valve and the pump and providing signals to operate the electro-mechanical valve and the pump in a controlled manner to selectively pump a predetermined quantity of liquid from the reservoir, through the flow restricting orifice and into the sterilizing chamber.

15. An unplumbed sterilizer comprising:

a reservoir holding a liquid and having a reservoir inlet and a reservoir outlet;

a sterilizing chamber for receiving a load to be sterilized and having a sterilizing chamber inlet for receiving the liquid;

a heater operatively connected to the sterilizing chamber for heating the liquid in the sterilizing chamber to create a sterilizing fluid;

a positive displacement pump having a pump inlet fluidly connected to the reservoir outlet;

a valve having a first valve port fluidly connected to a pump outlet and a second valve port fluidly connected to the sterilizing chamber inlet; and a controller operatively connected to the pump and providing signals to operate the pump in a controlled manner to selectively pump a predetermined quantity of liquid from the reservoir to the sterilizing chamber.

* * * * *